(12) United States Patent
Trigiante

(10) Patent No.: US 8,834,940 B2
(45) Date of Patent: Sep. 16, 2014

(54) COMPOSITIONS AND METHOD FOR HAIR LOSS PREVENTION

(75) Inventor: Giuseppe Trigiante, Pisa (IT)

(73) Assignee: Yagna Limited, London (GB)

( * ) Notice: Subject to any disclaimer, the term of this patent is extended or adjusted under 35 U.S.C. 154(b) by 1228 days.

(21) Appl. No.: 11/977,859

(22) Filed: Oct. 26, 2007

(65) Prior Publication Data

US 2008/0152731 A1    Jun. 26, 2008

Related U.S. Application Data

(60) Provisional application No. 60/854,810, filed on Oct. 27, 2006.

(51) Int. Cl.

| | | |
|---|---|---|
| A61K 36/00 | (2006.01) |
| A61K 9/08 | (2006.01) |
| A61K 31/505 | (2006.01) |
| A61K 9/00 | (2006.01) |
| A61K 31/435 | (2006.01) |
| A61K 31/555 | (2006.01) |
| A61K 45/06 | (2006.01) |
| A61K 36/61 | (2006.01) |
| A61Q 5/00 | (2006.01) |
| A61K 8/35 | (2006.01) |
| A61K 33/04 | (2006.01) |
| A61Q 7/00 | (2006.01) |
| A61K 8/33 | (2006.01) |
| A61K 8/27 | (2006.01) |
| A61K 8/37 | (2006.01) |
| A61K 31/496 | (2006.01) |
| A61Q 17/00 | (2006.01) |

(52) U.S. Cl.
CPC ............ *A61K 9/0014* (2013.01); *A61K 9/08* (2013.01); *A61K 31/505* (2013.01); *A61K 31/435* (2013.01); *A61K 31/555* (2013.01); *A61K 45/06* (2013.01); *A61K 36/61* (2013.01); *A61Q 5/006* (2013.01); *A61K 8/35* (2013.01); *A61K 33/04* (2013.01); *A61Q 7/00* (2013.01); *A61K 8/33* (2013.01); *A61K 8/27* (2013.01); *A61K 8/37* (2013.01); *A61K 31/496* (2013.01); *A61Q 17/005* (2013.01)
USPC ........................................................ 424/725

(58) Field of Classification Search
None
See application file for complete search history.

(56) References Cited

U.S. PATENT DOCUMENTS

| | | | |
|---|---|---|---|
| 5,183,817 A | 2/1993 | Bazzano et al. | |
| 2004/0191331 A1* | 9/2004 | Schwartz et al. | 424/641 |
| 2006/0029557 A1* | 2/2006 | Mitra et al. | 424/70.1 |
| 2007/0081967 A1* | 4/2007 | Cerullo et al. | 424/74 |

FOREIGN PATENT DOCUMENTS

| | | | |
|---|---|---|---|
| BE | 890708 A | * | 2/1982 |
| EP | 0249194 | | 12/1987 |
| EP | 0273202 | | 7/1988 |
| JP | 05286836 A | * | 11/1993 |
| WO | 86/04231 | | 7/1986 |
| WO | 97/12602 | | 4/1997 |
| WO | WO 2005067627 | * | 7/2005 |

OTHER PUBLICATIONS

Poulos, Investigational medications in the treatment of alopecia, Expert Opinion on Investigational Drugs, (Feb. 2005) vol. 14, No. 2, pp. 177-184.*

Wang et al, Interactions of the vitamin D receptor with the corepressor hairless: analysis of hairless mutants in atrichia with papular lesions, The Journal of biological chemistry, (Aug. 31, 2007) vol. 282, No. 35, pp. 25231-25239.*

Weiner et al, Hair lost in translation, Nature Genetics (2009), 41(2), 141-142) teach a new study identifies mutations in the HR gene as the cause of Marie Unna hereditary hypotrichosis (MUHH).*

Alopecia from Merck manuals, accessed on Mar. 4, 2010, pp. 1-4.*

Hartlapp et al, [Side-effects of polychemotherapy in metastatic testicular neoplasms (author's transl)]. Nebenwirkungen der Polychemotherapie bei metastasierten Hodentumoren, Klinische Wochenschrift, (Mar. 1, 1982) vol. 60, No. 5, pp. 257-261.*

Mols et al, Scalp cooling to prevent chemotherapy-induced hair loss: practical and clinical considerations, Supportive care in cancer : official journal of the Multinational Association of Supportive Care in Cancer, (Feb. 2009) vol. 17, No. 2, pp. 181-189.*

Whiting, The treatment of alopecia areata, Cutis; cutaneous medicine for the practitioner, (Sep. 1987) vol. 40, No. 3, pp. 247-250.*

Kalabokes et al, The role of the National Alopecia Areata Foundation in the management of alopecia areata, Dermatologic Therapy, (2001) vol. 14, No. 4, pp. 340-344.*

Rey et al, [Treatment of alopecia areata]. Tratamento da alopecia areata, Medicina Cutanea Ibero-Latino-Americana, (Mar. 2006) vol. 34, No. 2, pp. 49-56.*

Falbe et al. "ROMPP Lexikon Chemie." 1996, Georg Thieme Verlag, p. 241.

Kaufman, "Androgens and Alopecia." Molecular and Cellular-Endocrinology, 198: 89-95 (2002).

Choi et al. "Biochemical Roles of Testosterone and Epitestosterone to 5Alpha-Reductase as Indicators of Male-Pattern Baldness." J. Invest. Dermatol., 116(1): 57-61 (2001).

(Continued)

*Primary Examiner* — Qiuwen Mi
(74) *Attorney, Agent, or Firm* — MDIP LLC

(57) ABSTRACT

A formulation for hair loss prevention comprising at least one hair loss preventive ingredient known to inhibit the hormonal mechanism underlying androgenetic hair loss and a mixture of water and at least one aprotic organic solvent capable of solubilizing sebum and allowing the hair loss preventive ingredient to reach the skin and/or hair follicle, and methods of using the same.

13 Claims, No Drawings

(56) References Cited

OTHER PUBLICATIONS

Mercurio et al. "Androgen Physiology and the Cutaneous Pilosebaceous Unit." The Journal of Gender-Specific Medicine, 3(4): 59-64 (2000).

Stamatiadis et al, "Inhibition of 5Alpha-Reductase Activity in Human Skin by Zinc and Azelaic Acid." British Journal of Dermatology, 119(5): 627-632 (1988).

Olszewska et al., "Effective Treatment of Female Androgenic Alopecia with Dutasteride." Journal of Drugs in Dermatology, 4(5): 637-40 (2005).

Leyden et at., "Finasteride in the Treatment of Men with Frontal Male Pattern Hair Loss." Journal of the American Academy of Dermatology, 40(6, Part 1): 930-7 (1999).

Karam, "Topical Minoxidil Therapy for Androgenic Alopecia in the Middle East." International Journal of Dermatology, 32(10): 763-6 (1993).

Bazzano et al., "Topical Tretinoin for Hair Growth Promotion." Journal of the American Academy of Dermatology, 15 (4, Part 2): 880-883 and 890-893 (1986).

Habib et al. "Serenoa Repens (Permixon®) Inhibits the 5Alpha-Reductase Activity of Human Prostate Cancer Cell Lines without Interfering with PSA Expression." Int. J. Cancer 114: 190-4 (2005).

Holleran et. al. "Sphingolipids Are Required for Mammalian Epidermal Barrier Function." The Journal of Clinical Investigation, Inc., 88: 1338-1345 (1991).

Charnock et al. "Evaluation of the Antibacterial Efficacy of Diesters of Azelaic Acid." European Journal of Pharmaceutical Sciences, 21: 589-596 (2004).

\* cited by examiner

COMPOSITIONS AND METHOD FOR HAIR LOSS PREVENTION

CROSS-REFERENCE TO RELATED APPLICATION

This application claims the benefit of U.S. provisional application Ser. No. 60/854,810, filed Oct. 27, 2006, hereby incorporated by reference.

FIELD OF THE INVENTION

The invention pertains to the field of hair loss prevention using a formulation endowed with the ability to reach the papilla and deliver a drug that will encourage hair growth, therefore resulting in prevention and arrest of male pattern baldness (androgenetic alopecia) in human subjects; and a method for the application of the formulation in order to achieve scalp degreasing, dandruff removal or hair loss prevention.

BACKGROUND OF THE INVENTION

Androgenetic alopecia (AGA) is a genetically based disorder of the scalp, which results in gradual and permanent miniaturization of the hair follicles on regions of the scalp ultimately resulting in baldness. This condition, while not life threatening, is psychologically highly devastating in affected people and can result in depression and poor quality of life.

Research has shown that the phenomenon is connected to the male hormone testosterone. Kaufman, K D, "Androgens and alopecia," *Mol. Cell. Endocrinol.*, 198(1-2), 89-95 (2002). Women and men with low levels of testosterone are less susceptible to AGA. Yet testosterone by itself is not sufficient to trigger the process. The process requires an additional step of chemical transformation in order to be effective. This additional process was shown to be the testosterone reduction to dihydrotestosterone (DHT), the ultimate baldness effector. Choi et al., "Biochemical roles of testosterone and epitestosterone to 5 alpha-reductase as indicators of male-pattern baldness," *J. Invest. Dermatol.*, 116(1), 57-61 (2001).

The conversion occurs in the body by means of the enzyme 5α-reductase, which is abundant in the skin and follicles of susceptible individuals. It is this same hormone that stimulates sebaceous glands, located in hair follicles, to produce sebum which is then secreted onto the skin. An excessive sebum production is known as seborrhoea and is often associated with AGA. Mercurio et al., "Androgen physiology and the cutaneous pilosebaceous unit," *J. Gend. Specif. Med.*, 3(4), 59-64 (2000). Seborrhoea exacerbates the effects of balding because it causes stickiness of hair and favours the production of dandruff.

Dandruff itself (*Pityriasis capitis*) is another relevant problem for balding individuals and a potential source of stress and social embarrassment. It is due to an excessive turnover of scalp skin which in turn results in copious shedding of whitish flakes. The cause of dandruff has been identified in the fungus *Malassezia globosa* which metabolises scalp triglycerides (sebum) into oleic acid which is an irritant and provokes the turnover increase. Therefore, the three problems mentioned are all connected and tend to afflict overlapping groups of individuals.

Many compounds to date have been shown to inhibit DHT formation from testosterone, such as finasteride, dutasteride, zinc, and azelaic acid. See, Stamatiadis, et al. "Inhibition of 5 alpha-reductase activity in human skin by zinc and azelaic acid," *Br. J. Dermatol.* 119(5), 627-32 (1988); Olszewska et al., "Effective treatment of female androgenic alopecia with dutasteride," *J. Drugs Dermatol.*, 4(5), 637-40 (2005); and Leyden et al., "Finasteride in the treatment of men with frontal male pattern hair loss," *J. Am. Acad. Dermatol.*, 40(6 Pt 1), 930-7 (1999). Of these, finasteride has been licensed for commercial use for the purpose of preventing AGA.

Many other compounds have been shown to stimulate hair growth by yet unclear mechanisms which may be connected to increased blood supply to the follicle and stimulated cell proliferation. These include minoxidil and tretinoin. See, Karam P., "Topical minoxidil therapy for androgenic alopecia in the Middle East. The Middle-Eastern Topical Minoxidil Study Group," *Int. J. Dermatol.*, 32(10), 763-6 (1993); and Bazzano et al., "Topical tretinoin for hair growth promotion," *J. Am. Acad. Dermatol.*, 15(4 Pt 2), 880-883 and 890-893 (1986). Minoxidil has been licensed for commercial use for the treatment of AGA.

The saw palmetto extract is a common herbal supplement taken orally and known to be beneficial in enlarged prostate patients. Medical research has shown that it is a good inhibitor of 5α-reductase, the enzyme responsible for generating DHT, the harmful form of testosterone. See, Habib, F. K., et al. "Serenoa repens (Permixon) inhibits the 5 alpha-reductase activity of human prostate cancer cell lines without interfering with PSA expression", *Int. J. Cancer* 114 (2), 190-4 (2005). It is widely available, taken systemically, and has a good safety record. The only common remedy for sebum overproduction is detergency. To this date, there are no topical formulas with a proven capacity to reduce sebum production, therefore, the only option is sebum removal once produced. There are many detergents available, but they all come with the drawback that a rinse is required to flush them and so access to water and hair drying equipment is necessary. For dandruff prevention fighting the responsible fungus will dramatically alleviate the condition. Many antifungal compounds are used cosmetically as additives to shampoos, including zinc pyrithione, tar, selenium sulfide, and ketoconazole. These compounds all have a long usage history which has proven they are effective and safe to use.

The prior art relates to treatment of the hair strands themselves (such as thickening) and not skin penetration. Moreover, there is no intent to deliver active ingredients to hair follicles or to treat sebum. The present invention is directed to addressing the need for compositions that remove excess sebum and dandruff while also stimulating hair growth.

SUMMARY OF THE INVENTION

One embodiment of the invention encompasses formulations for hair loss prevention comprising an aprotic organic solvent/water mixture and at least one hair loss preventive ingredient known to inhibit the hormonal mechanism underlying androgenetic hair loss. The aprotic organic solvent may be an ester, aldehyde, or ketone. Typically, the aprotic organic solvent may have $C_2$-$C_{10}$ atoms. The aprotic organic solvent may be present in an amount of 60% to 90% by weight of the formulation. The water may be present in an amount of 2% to 20% by weight of the formulation.

The hair loss preventive ingredient may be a $C_6$-$C_{14}$ dicarboxylic acid, finasteride, minoxidil, tretinoin, or a herbal extract. Preferably, the $C_6$-$C_{14}$ dicarboxylic acid is azelaic acid. When the hair loss preventive ingredient is azelaic acid, it is present in an amount of about 2% to 30% by weight of the formulation and preferably between 10% and 25% by weight. Preferably, the herbal extract is saw palmetto extract. When the hair loss preventive ingredient is saw palmetto extract, it is present in an amount of about 0.5% to 5% by weight of the formulation. When the hair loss preventive ingredient is finasteride, minoxidil, or tretinoin, it is present in an amount of about 0.001% to 5% by weight of the formulation. The composition may further comprise at least one antifungal compound. Preferably, the antifungal compound include zinc pyrithione, tar, selenium sulfide, ketoconazole, or tea tree oil. When the antifungal compound is zinc pyrithione, it is present in an amount of about 0.001% to 5% by weight of the formulation.

Another embodiment of the invention encompasses a method to prevent hair loss and degrease the scalp comprising applying a hair loss prevention formulation in a therapeutically sufficient amount to an area of skin and massaging the area of skin until the formulation is absorbed through the skin, wherein hair loss prevention formulation has an aprotic organic solvent/water mixture and at least one hair loss preventive ingredient known to inhibit the hormonal mechanism underlying androgenetic hair loss.

DETAILED DESCRIPTION OF THE INVENTION

The invention is directed to formulations that address both the problem of seborrhoea and of AGA. Thus, the invention relates to the cosmetic field of hair loss prevention, dandruff removal, and/or scalp cleansing. Not to be limited by theory, however, it is believed that the solvent mixture of the composition, which has the same lipophilicity as the scalp itself, interacts with the scalp in such a manner as to dissolve the sebum layer which covers the scalp in individuals affected by excessive sebum production (greasy skin) and allows for the efficient penetration of the active ingredients into the skin and/or hair follicles. It is these active ingredients in the formulation, which are known in the literature to interfere with the hormonal mechanisms underlying androgenetic alopecia (male hair loss), that prevent hair loss. In addition, the formulation ensures that dandruff production is slowed to normal levels.

Thus, the formulation for the prevention of hair loss comprises a solvent/water mixture and at least one hair loss preventive ingredient, wherein the solvent/water mixture is capable of solubilizing sebum and allowing the hair loss preventive ingredient to reach the skin and/or hair follicle. The formulations may be in the form of a gel, paste, cream, lotion, or ointment, or on a carrier (e.g. on sponges, in dispensers or cotton applicators).

The solvent/water mixture is a mixture of water and at least one solvent that can solubilize sebum (grease). The purpose of sebum is to provide the skin with a waterproof barrier to prevent microbial invasion, however, sebum itself is a combination of fatty acids and esters which are quite insoluble in water and usually require the use of surfactants (i.e., shampoo) for removal. The solvent should effectively dissolve the sebum layer and temporarily create a permeability breach in the skin (or upper epidermis). An advantage of the composition over existing ones is its unique lipophilicity which allows its active ingredients (which are mostly lipophilic) to be dissolved in higher amounts than would be possible in aqueous based solutions and effectively penetrate through the skin. Other solvents with this capacity can be found in the literature. See, Holleran et. al., "Sphingolipids Are Required for Mammalian Epidermal Barrier Function," *J. Clin. Investigation, Inc.*, 88, 1338-1345 (1991), hereby incorporated by reference.

The solvent/water mixture is a mixture of water and at least one aprotic solvent. Typically, the aprotic organic solvent includes, but is not limited to, an ester, aldehyde, or ketone. Typically, the organic solvent has $C_2$-$C_{10}$ atoms. Preferably, the esters have $C_2$-$C_6$ atoms. More preferably, the ester is methyl formate, ethyl formate, propyl formate, methyl acetate, ethyl acetate, propyl acetate, methyl propionate, ethyl propionate, or propyl propionate. Most preferably, the ester is ethyl acetate. Preferably, the aldehydes have $C_2$-$C_4$ atoms. More preferably, the aldehyde is acetaldehyde, propionaldehyde, or butyraldehyde. Most preferably, the aldehyde is propionaldehyde. Preferably, ketones have $C_3$-$C_6$ atoms. More preferably, the ketone is acetone, butanone, pentanone, ethylisopropyl ketone, or methylisobutyl ketone. Most preferably, the ketone is acetone.

Typically, the aprotic organic solvent is present in an amount of 60% to 90% by weight of the formulation. The water is present in an amount of 2% to 20% by weight of the formulation.

The hair loss preventive ingredient should prevent hair loss, and may also promote hair growth. The hair loss preventive ingredients can be an inhibitor of DHT production and therefore an inhibitor of the mechanism underlying hair loss. See Stamatiadis, et al. "Inhibition of 5 alpha-reductase activity in human skin by zinc and azelaic acid," *Br. J. Dermatol.* 119(5), 627-32 (1988), hereby incorporated by reference. Other ingredients may be known to promote hair growth. For example, see Bazzano et al., "Topical tretinoin for hair growth promotion," *J. Am. Acad. Dermatol.*, 15(4 Pt 2), 880-833 and 890-893 (1986). Typically, hair loss preventive ingredients include, but are not limited to, a $C_6$-$C_{14}$ dicarboxylic acid, finasteride, minoxidil, tretinoin, or a herbal extract. Dicarboxylic acids are very soluble in the solvent/water mixture and once on the skin act as sebum absorbing particles which further reduce the oiliness of the skin. Therefore, they may play a double role in the formulation as a hair loss preventive ingredient and as a sebum reducing agent. Other dicarboxylic acids, such as azelaic acid, may act as an antibacterial agent which helps maintain a satisfactory hygiene level in the scalp and therefore prevents irritation and itchiness often associated with seborrhoea. See, Charnock et al., "Evaluation of the antibacterial efficacy of diesters of azelaic acid," *Eur. J. Pharm. Sci.*, 21(5), 589-96 (2004).

Preferably, the $C_6$-$C_{14}$ dicarboxylic acid is pimelic acid, suberic acid, azelaic acid, sebacic acid, undecanedioic acid, dodecanedioic acid, or brassylic acid. Preferably, the herbal extract is saw palmetto extract. This extract is oil based and easily soluble in the composition.

The composition may further comprise at least one of antifungal compound. Preferably, the antifungal compound include, but are not limited to, zinc pyrithione, tar, selenium sulfide, ketoconazole, or tea tree oil.

When the hair loss preventive ingredient is a dicarboxylic acid, it is present in an amount of about 2% to 30% by weight of the formulation and preferably between 10% and 25% by weight. When the hair loss preventive ingredient is saw palmetto extract, it is present in an amount of about 0.5% to 5% by weight of the formulation. When the hair loss preventive ingredient is finasteride, minoxidil, or tretinoin, it is present in an amount of about 0.001% to 5% by weight of the formulation. Additionally, when the antifungal compound is zinc pyrithione, it is present in an amount of about 0.001% to 5% by weight of the formulation.

These composition may contain one or more preservatives, coloring agents, anti-oxidants, water, acids, buffering agents, emulsifying agents, thickeners, solvents, perfuming agents, and the like, and mixtures thereof.

Preservatives may include, but not limited to, tetrasodium ethylene-diamine tetraacetic acid (EDTA), methylparaben, benzophenone-4, methylchloroisothiazolinone, methylisothiazolinone, and the like, and mixtures thereof. Preservatives, when used, are typically present in an amount from about 0.01% to 6% by weight of the formulation, preferably about 0.05% to 4%, and more preferably from about 0.1% to 2% by weight of the formulation.

Coloring agents may include, but not limited to, FD&C Green No. 3, Ext. D&C Violet No. 2, FD&C Yellow No. 5, FD&C Red No. 40, and mixtures thereof. The coloring agents, when used, are typically present in an amount from about 0.001% to 0.1% by weight of the formulation, and preferably from about 0.005% to 0.05% by weight of the formulation.

The formulation may further comprise anti-oxidants, both the enzymatic and non-enzymatic type. For example, superoxide dismutase (SOD), catalase, and glutathione peroxidase are natural enzymatic anti-oxidants used by the body that may be supplemented with the compositions herein. Suitable non-enzymatic anti-oxidants may include, but not limited to, Vitamin E (e.g., tocopherol), Vitamin C (ascorbic acid), carotenoids, Echinacoside and caffeoyl derivatives, oligomeric proanthocyanidins or proanthanols (e.g., grape seed extract), silymarin (e.g., milk thistle extract, Silybum marianum), *ginkgo biloba*, green tea polyphenols, and mixtures thereof. Carotenoids are powerful anti-oxidants, and they may include beta-carotene, canthaxanthin, zeaxanthin, lycopen, lutein, crocetin, capsanthin, and the like. Indeed, any pharmaceutically acceptable compounds suitable for administration orally or topically may be used as an anti-oxidant in the compositions. The anti-oxidant component, when used, is present in an amount sufficient to inhibit or reduce the effects of free-radicals at the scalp. The anti-oxidant component may be present in an amount from about 0.001 to 1 weight percent of the composition.

The invention encompasses a method of preventing hair loss comprising applying a hair loss prevention formulation in a therapeutically sufficient amount to an area of skin and massaging the area of skin until the formulation is absorbed through the skin, wherein the formulation comprises a water/solvent mixture and at least one hair loss preventive ingredient known to inhibit the hormonal mechanism underlying androgenetic hair loss. The solvent is at least one aprotic organic solvent and the hair loss preventive ingredient are those described above. The formulation may further comprise at least one antifungal compound, such as those described above.

Having described the invention with reference to certain preferred embodiments, other embodiments will become apparent to one skilled in the art from consideration of the specification. The invention is further defined by reference to the following example describing in detail the formation of the formulations for the hair loss prevention. It will be apparent to those skilled in the art that many modifications, both to materials and methods, may be practiced without departing from the scope of the invention.

EXAMPLES

Example 1

The following ingredients were mixed using technology commonly available to the skilled artisan to obtain the formulation described below.

| Ingredient | Amount (g) | Percentage w/w |
| --- | --- | --- |
| Acetone | 25.3 | 76% |
| Water | 1.7 | 5% |
| Azelaic acid | 6.7 | 20% |
| Tretinoin | 0.015 | 0.05% |

Example 2

The following ingredients were mixed using technology commonly available to the skilled artisan to obtain the formulation described below.

| Ingredient | Amount (g) | Percentage w/w |
| --- | --- | --- |
| Acetone | 25.3 | 76% |
| Water | 1.7 | 5% |
| Azelaic acid | 5.9 | 17% |
| Tretinoin | 0.015 | 0.05% |
| Minoxidil | 0.7 | 2% |
| Finasteride | 0.07 | 0.2% |

Example 3

The following ingredients were mixed using technology commonly available to the skilled artisan to obtain the formulation described below.

| Ingredient | Amount (g) | Percentage w/w |
| --- | --- | --- |
| Acetone | 25.3 | 76% |
| Water | 1.7 | 5% |
| Pimelic acid | 3.3 | 10% |
| Suberic acid | 3.3 | 10% |
| Saw Palmetto Extract | 0.33 | 1% |
| Zinc pyrithione | 0.015 | 0.05% |

Example 4

The following ingredients (using other dicarbxylic acid with similar properties) were mixed using technology commonly available to the skilled artisan to obtain the formulation described below.

| Ingredient | Amount (g) | Percentage w/w |
| --- | --- | --- |
| Acetone | 25.3 | 76% |
| Water | 1.7 | 5% |
| Azelaic acid | 5.9 | 17% |
| Zinc pyrithione | 0.015 | 0.05% |
| Minoxidil | 0.7 | 2% |
| Finasteride | 0.07 | 0.2 |

Example 5

The following ingredients were mixed using technology commonly available to the skilled artisan to obtain the formulation described below.

| Ingredient | Amount (g) | Percentage w/w |
| --- | --- | --- |
| Acetone | 25.3 | 76% |
| Water | 1.7 | 5% |

| Ingredient | Amount (g) | Percentage w/w |
| --- | --- | --- |
| Azelaic acid | 5.9 | 17% |
| Ketoconazole | 0.3 | 1% |
| Minoxidil | 0.7 | 2% |
| Finasteride | 0.07 | 0.2 |

What is claimed is:

1. A fomulation to treat hair loss comprising at least one ingredient known to inhibit the hormonal mechanism underlying androgenetic hair loss, a $C_6$-$C_{14}$ dicarboxylic acid, and a mixture of water and at least one aprotic organic solvent, wherein the mixture of water and aprotic organic solvent is capable of solubilizing sebum and allowing the at least one ingredient to reach the skin and/or hair follicle, and wherein the aprotic organic solvent is present in an amount of 60% to 90% by weight of the formulation and the water is present in an amount of 2% to 20% by weight of the formulation.

2. The formulation according to claim 1, wherein the aprotic organic solvent is selected from the group consisting of esters, aldehydes, ketones and mixtures thereof.

3. The formulation according, to claim 2, wherein the ketone is a $C_2$-$C_6$ ketone.

4. The formulation according to claim 2, wherein the ester is methyl formate, ethyl formate, propyl formate, methyl acetate, ethyl acetate, propyl acetate, methyl propionate, ethyl propionate or propyl propionate.

5. The formulation according to claim 2, wherein the aldehyde is acetaldehyde, propionaldehyde or butyraldehyde.

6. The formulation according to claim 2, wherein the ketone is acetone, butanone, pentarione, ethylisopropyl ketone, or methylisobutyl ketone.

7. The formulation according to claim 1, wherein the dicarboxylic acid is pimelic acid, suberic acid, azelaic acid, sebacic acid, undecanedioic acid, dodecanedioic acid, or brassylic acid.

8. The formulation according to claim 7, wherein the dicarboxylic acid is present in an amount of about 2% to 30% by weight of the formulation.

9. The formulation according to claim 7, wherein the at east one ingredient is azelaic acid.

10. The formulation according to claim 1, further comprising at least one antifungal compound.

11. The formulation according to claim 10, wherein the antifungal compound is selected from the group consisting of zinc pyrithione, tar, selenium sulfide, ketoconazole, tree oil and combinations thereof.

12. The formulation according to claim 1, wherein the formulation further comprises minoxidil.

13. A formulation to treat hair loss comprising: acetone in 76% by weight of the formulation, water in 5% by weight of the formulation, azelaic acid in 17% by weight of the formulation, zinc pyrithione in 0.05% by weight of the formulation, minoxidil in 2% by weight of the formulation, and finasteride in 0.2% by weight of the formulation, wherein the mixture of water and acetone is capable of solubilizing sebum and allowing the formulation to reach the skin and/or hair follicle.

* * * * *